United States Patent [19]

Sinofsky et al.

[11] Patent Number: 5,135,001
[45] Date of Patent: Aug. 4, 1992

[54] ULTRASOUND SHEATH FOR MEDICAL DIAGNOSTIC INSTRUMENTS

[75] Inventors: Edward L. Sinofsky, Peabody; Barry D. Weitzner, Chelmsford, both of Mass.

[73] Assignee: C. R. Bard, Inc., Murray Hill, N.J.

[21] Appl. No.: 622,513

[22] Filed: Dec. 5, 1990

[51] Int. Cl.⁵ .............................................. A61B 8/14
[52] U.S. Cl. .................... 128/662.06; 128/662.03
[58] Field of Search ............... 128/662.03, 662.06, 128/662.04

[56] References Cited

U.S. PATENT DOCUMENTS

| | | | |
|---|---|---|---|
| 3,430,625 | 3/1969 | McCleod | 128/662.06 |
| 3,779,234 | 12/1973 | Eggleton et al. | 128/2 |
| 3,938,502 | 2/1976 | Bom | 128/662.06 |
| 4,176,662 | 12/1979 | Frazer | 128/662.06 |
| 4,354,500 | 10/1982 | Colley et al. | 128/662.06 |
| 4,462,408 | 7/1984 | Silverstein et al. | 128/660 |
| 4,561,446 | 12/1985 | Hetz | 128/662.06 |
| 4,587,972 | 5/1986 | Morantte, Jr. | 128/660 |
| 4,593,699 | 6/1986 | Poncy et al. | 128/662.03 |
| 4,665,925 | 5/1987 | Millar | 128/662.06 |
| 4,690,131 | 9/1987 | Lyddy, Jr. et al. | 128/4 |
| 4,697,595 | 10/1987 | Breyer et al. | 128/662.06 |
| 4,744,368 | 5/1988 | Young et al. | 128/662.04 |
| 4,763,662 | 8/1988 | Yokoi | 128/660 |
| 4,771,788 | 9/1988 | Millar | 128/662.06 |
| 4,779,624 | 10/1988 | Yokoi | 128/660.06 |
| 4,815,470 | 3/1989 | Curtis et al. | 128/662.03 |
| 4,815,479 | 3/1989 | Curtis et al. | 128/662.03 |
| 4,841,977 | 6/1989 | Griffith et al. | 128/660.03 |
| 4,972,839 | 11/1990 | Angelsen | 128/662.06 |

FOREIGN PATENT DOCUMENTS

| | | |
|---|---|---|
| WO89/04143 | 5/1989 | European Pat. Off. . |
| 2157828A | 10/1985 | United Kingdom . |
| 2208138 | 3/1989 | United Kingdom ........... 128/662.06 |

Primary Examiner—Francis Jaworski
Assistant Examiner—George Manuel
Attorney, Agent, or Firm—Darby and Darby

[57] ABSTRACT

A flexible disposable ultrasound transducer sheath for medical diagnostic instruments comprises a core having a central opening aligned to a core axis and contoured and dimensioned in cross section in correspondence with the cross section of a standard instrument shaft where the transducer is to be removably applied. A piezoelectric layer of flexible polyvinylidene fluoride is formed over the core and a first electrically conductive gold layer electrode is sandwiched between the piezoelectric layer and the outer core surface. A second conductive layer is formed over the piezoelectric layer and includes a plurality of conductive gold strip electrodes aligned with the axis of the core, the strips being separated one from the other circumferentially. The transducer, when driven with electrical pulses, is an ultrasound emitter. As a receiver, the transducer converts returning echoes into electrical signals. Alternative embodiments include inflatable balloons over the transducer or as an element of the transducer.

28 Claims, 2 Drawing Sheets

ULTRASOUND SHEATH FOR MEDICAL DIAGNOSTIC INSTRUMENTS

FIELD OF THE INVENTION

This invention relates generally to instruments that can be inserted into body lumens or cavities, and more particularly to instruments having capability for ultrasound imaging.

BACKGROUND OF THE INVENTION

Ultrasound energy is commonly used for imaging of internal body structures. Endoscopes are used for visual inspection of internal organs of living bodies. Endoscopes and catheters incorporating ultrasound transducers are well known. The instruments typically include a flexible tube that extends between a control housing at the proximal end and a probe at its distal end. The probe is controlled by an operator, and illumination and viewing means are usually provided in the system.

When optical means are used to view the interior surfaces of the body cavities through which the endoscope passes, the operator receives information concerning only interior surface conditions. Ultrasonics provide subsurface imaging information of underlying structure and interior organs. Thus, it is desirable to have both optical viewing and ultrasonic information at a desired location within a patient's body.

However, many current ultrasound devices may require that other functions, for example, the viewing function, be compromised to accommodate the ultrasound function. The increased costs and the possibility of interfering with an existing instrument capability by the combination with ultrasound imaging are two factors that have tended to limit usage of instruments with ultrasound imaging capability. Nevertheless, instruments lacking ultrasonic capability have little relative value when compared to a similar instrument with ultrasound capability. Therefore, upgrading is desirable for many existing instruments now lacking ultrasound capability.

It would be advantageous to have an ultrasonic imaging capability even when the instrument is otherwise a non-electrical device. For example, conventional catheters and dilators would be good vehicles for the addition of ultrasound capability.

What is needed is a low cost device for adding ultrasound imaging capability to existing instruments now used, without imaging, to perform diagnostic functions within body cavities.

BRIEF DESCRIPTION OF THE INVENTION

Accordingly, an object of the invention is to provide an improved ultrasound sheath for attachment to medical diagnostic instruments, enabling performance of an additional function.

Another object of the invention is to provide an improved ultrasound sheath for medical diagnostic instruments that can be added to existing diagnostic instruments without alterations of the initial device.

Still another object of the invention is to provide an improved ultrasound sheath for medical diagnostic instruments that is disposable after use and economical to produce and utilize.

Yet another object of the invention is to provide an improved ultrasound sheath for medical diagnostic instrument, that is combinable with existing endoscopes, catheters, dilators, and the like.

In a preferred embodiment of an ultrasound sheath for medical diagnostic instruments in accordance with the invention, the transducer comprises a core having a central opening aligned to a core axis. The central opening is contoured and dimensioned in cross section transverse to the axis in correspondence with the cross section of the instrument shaft where the transducer is to be applied. A resilient piezoelectric layer is formed over the core and a first electrically conductive gold layer is sandwiched between the piezoelectric layer and the outer surface of the core. The first conductive layer makes good surface contact with both the core and the piezoelectric layer. A second conductive layer is formed over the outside of the piezoelectric layer and includes a plurality of conductive gold strips aligned with the axis of the core, the strips being separated one from the other circumferentially. The transducer when driven with electrical pulses, is an ultrasound emitter. As a receiver, the transducer converts returning echoes into electrical signals.

Alternative embodiments in accordance with the invention include inflatable balloons over the transducer or as an element of the transducer. When the diagnostic instrument is properly positioned in the body of a subject, the balloon is inflated to provide better contact and more efficient energy transmission between the transducer and the body tissues.

Further objects and advantages of the invention will be apparent from the specification and drawings. The invention accordingly, comprises the features of construction, combination of elements, and arrangement of parts that will be exemplified in the constructions hereinafter set forth, and the scope of the invention will be indicated in the appended claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
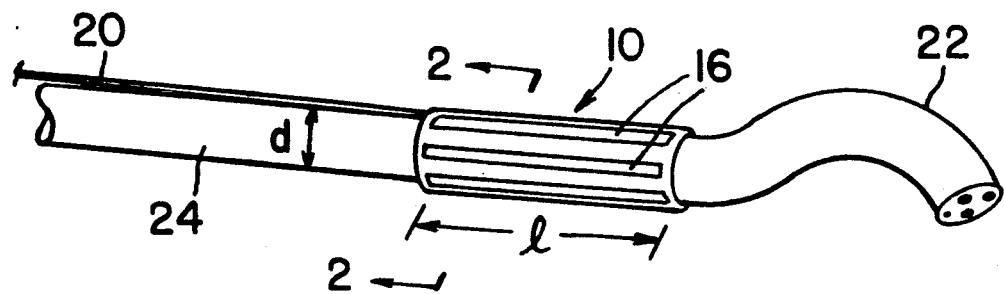
FIG. 1, is a perspective view of an ultrasound sheath for medical diagnostic instruments in accordance with the invention, applied to an endoscope.

With regard to FIG. 1, and ultrasound sheath 10 in accordance with the invention includes an electrically insulating cylindrical core 11 having a thin layer 12 of gold and an overlying flexible piezoelectric element 14 formed thereon, the core 11, gold layer 12 and piezoelectric element 14 being substantially coaxial and coextensive.

A plurality of gold electrodes 16 are formed on the outer surface of the piezoelectric element 14 and extend generally parallel to the longitudinal axis 18 of the core 11. The electrodes 16 are spaced apart circumferentially, with each electrode 16 approximately the same distance from the adjacent electrodes. It should be understood that in an alternative embodiment of the sheath 10, circumferential spacing may not be uniform so as to obtain desired directional effects, and the lengths of the electrodes 16 on the piezoelectric element 14 may also not be uniform.

A plurality of leads 20, electrical conductors, extend from one end of the sheath 10. A single lead 20 connects to each longitudinal electrode 16 and to the gold layer 12 such that an electrical potential may be applied between the cylindrical ground electrode 12 and each longitudinal electrode 16, respectively. In use, the electrical signals are provided and processed by external electronic circuits and devices (not shown) that are known in the art. Similarly, techniques for attaching fine leads to such thin electrodes are also well known.

It is a well-known phenomenon that the piezoelectric material 14 is elastically distorted, that is, changed dimensionally, when an electric potential is applied across the piezoelectric material 14. A voltage applied between any single longitudinal electrode 16 and the gold layer 12 creates a local distortion in the piezoelectric material 14, which distortion is released when the voltage is removed. Any number of longitudinal electrodes 16 can be connected simultaneously to the source of electrical voltage. When all of the electrodes 16 are simultaneously powered, an omnidirectional acoustic output is provided. Directionally lobed outputs can be provided by selection of the electrodes 16 that are powered, and their sequence of energization.

Pulsing of the electrodes 16 provides a physical output of the same fundamental frequency as the energizing pulses. Waves of ultrasonic energy are directed radially outward from the longitudinal axis 18. The relative rigidities of the internal core 11, the endoscope to which the sheath 10 is applied, and the elastic, resilient piezoelectric material 14, assure that substantially all of the ultrasonic energy is reflected at the core/electrode interface with the resilient piezoelectric material and directed radially outward.

The electrodes 12, 16, may be formed on the cylinder of piezoelectric material 14 by conventional techniques, for example, vapor deposition or sputtering, and the spaces between the longitudinal electrodes 16 can be formed, for example, by ablating portions of the outer surface with a laser beam.

The inside diameter of the core 11 is selected to provide a precision fit on the body or shaft of a standard endoscope 22, or the shaft of any other instrument, for example, a dilator, catheter, etc. To add an ultrasonic capability to the conventional endoscope, the sheath 10 is slid along the cylindrical shaft 24 of the endoscope 22 using, for example, water on the surface as a lubricant. In the process of positioning the sheath 10, the sheath may be rotated about the axis 18, to achieve the desired alignment relative t the tip of the instrument. Because the endoscope is flexible to allow bending, it is necessary that the sheath 10 also be bendably flexible. The very thinness of the layers 11, 12, 14, 16 as discussed hereinafter produces the required bendability although the core and electrode materials, if considerably thicker, would be considered to be rigid materials.

Further, although the sheaths illustrated in the figures have axial lengths 1 greater than their diameters d, it should be understood that in alternative embodiments in accordance with the invention, the axial length of a sheath may be equal to or less than the diameter. Reducing the 1/d ratio improves the ability of the sheath to bend with the endoscope shaft in use and in application of the sheath to the instrument.

The piezoelectric element 14 may be formed of a resilient composition of polyvinylidene fluoride (PVDF), which is a known piezoelectric polymer when prepared in a known manner, for example, in an electric field at elevated temperature. As is well known, piezoelectric elements when driven by electrical impulses are emitters of sonic energy. On the other hand, forces acting on the surface of the piezoelectric element induce distortions that in turn induce measurable electrical potentials between the ground electrode 12 and the longitudinal electrodes 16. Thus, a sheath 10 that serves as an ultrasound emitter can also be adapted electronically for receiving returning echoes of the emitted sounds. Control of emitting frequencies, for example, in the order of 40 MHz, and pulse width to achieve desired image resolutions, are techniques well known in the ultrasonic instrumentation arts.

The sheath 10 is very thin and therefore is flexible even though, as stated, the core 11 and gold electrodes, if much thicker, might be considered as rigid. The sheath 10 is readily removed from the endoscope 22, e.g., by peeling and cutting, for replacement with another sheath 10. Mounting the sheath 10 on the shaft 24 of the endoscope 22, provides a rigid backing for the piezoelectric emitter/receiver and further assures efficient outward energy emission and reception with minimal energy loss. Thus, a disposable ultrasound device and ultrasound capability are provided for application to conventional endoscopes. The sheaths are produced economically using known techniques as indicated above.

The resilient piezoelectric layer 14 may have a thickness in the range of 5 to 15 microns. The core, which may be fabricated of vinyl, polyethylene, polyurethane, and the like, has a thickness in the range of 150 to 250 microns, and the gold electrodes may have a thickness less than a micron.

Figure 3:
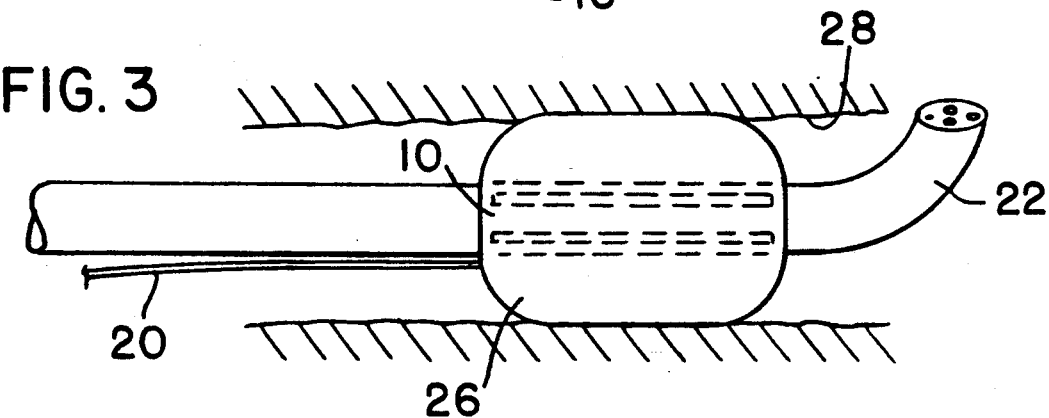
FIG. 3, is an alternative embodiment of an ultrasound sheath for medical diagnostic instruments in accordance with the invention including a fluid-filled balloon.

FIG. 3, illustrates the ultrasonic sheath 10 of FIG. 1, to which is attached an inflatable balloon 26. After the endoscope 22 is positioned within the subject's body at the desired location with the balloon 26 deflated, the balloon 26 is filled with liquid by known techniques such that good contact is made between the outside surface of the balloon 26 and the internal surfaces 28 of the living body. Such firm contact between the balloon and the body surfaces 28 assures more efficient transmission and echo reception of ultrasound energy at the sheath 10 than would be provided when gaps and spaces exist between the ultrasound sheath and the body tissues.

Figure 2:
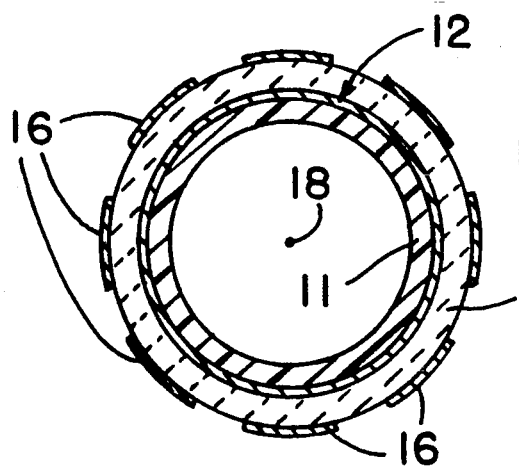
FIG. 2, is a sectional view to an enlarged scale taken along the line 2—2 of FIG. 1.
Figure 4:
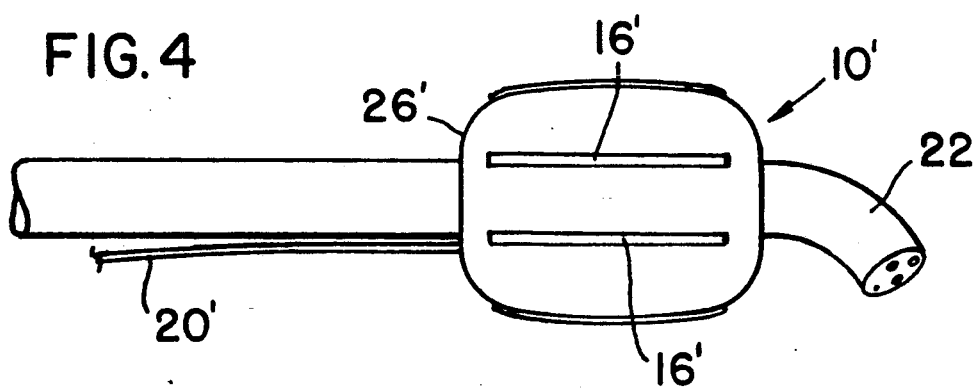
FIG. 4, is another alternative embodiment of an ultrasound sheath for medical diagnostic instruments in accordance with the invention including an inflatable balloon.

FIG. 4 illustrates an ultrasonic sheath 10' that is similar to the sheaths 10 of FIGS. 1-3. In this embodiment in accordance with the invention, the longitudinal electrodes 16' are mounted on the outside surface of a balloon 26'. The balloon 26' envelops the central cylindrical gold electrode 12 and piezoelectric element 14 (not shown in FIG. 4). As in the other embodiments, electrical leads (not shown) connect to each longitudinal electrode 16' so that ultrasonic emission and reception is achieved, as described above. The endoscope 22 is inserted within the body with the balloon 26' deflated. The balloon 26' is inflated at the desired body location to provide good surface contact and efficient transmission and reception of ultrasonic energy. In ,an alternative embodiment, the electrodes 16' may be on the inside surface of the balloon 26'.

It should be understood that in alternative embodiments in accordance with the invention, the longitudinal strip electrodes 16 and continuous cylinder electrodes 12 ca be reversed in position, that is, the electrodes 16 are positioned closer to the endoscope 22 and the continuous cylindrical electrode 12 is away from the endoscope shaft 24. Further, the electrode 12 may also be divided into separated strips, segments, and the like. The electrodes 12, 16 may also be divided in the longitudinal direction and in patterns to suit a desired objective. Each electrode segment in use is connected by a lead directly or indirectly to a driving signal generating/data processing system external to the human body.

Figure 5:
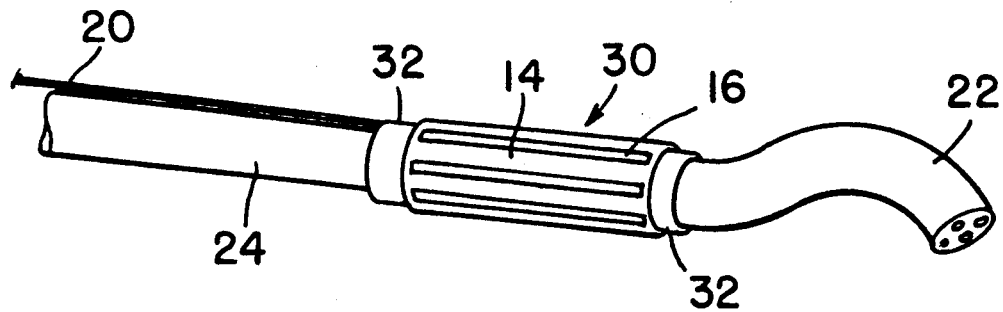
FIG. 5, is a view similar to FIG. 1, of an alternative embodiment of an ultrasound sheath for medical diagnostic instruments in accordance with the invention.

In FIG. 5, a sheath 30 is similar to the sheath 10 of FIGS. 1 and 2, with the addition of flexible cuffs 32, having resilience and a greater flexibility than the piezoelectric element 14. By known techniques, for example, double injection molding, such cuffs 32 of greater resilience and elasticity than the combined core and transducing layers 12, 14, 16 of the sheath 30, may be provided. The unstressed internal diameter of the cuffs 32 is smaller than the shaft diameter of the endoscope 22, such that in sliding the sheath 30 onto the endoscope 22, a very tight fit is achieved between the cuffs 32 and the shaft 24. A precision fit is not required between the core 11 and the shaft 24. As stated, the relative rigidity of the internal core and inner electrode 12 assures efficient outward radiation of ultrasonic energy and efficient reception of returning echoes, without undue absorption losses.

Figure 6:
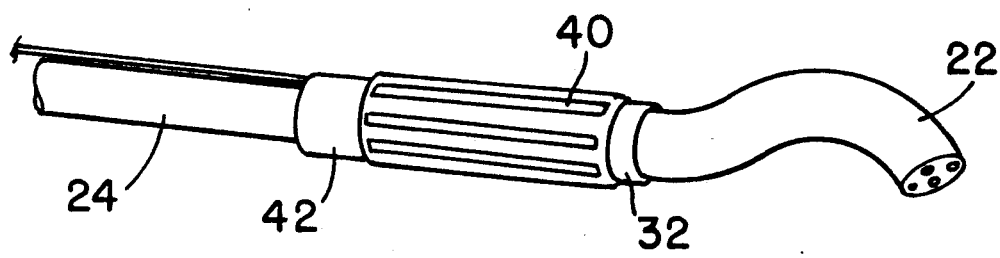
FIG. 6, is still another alternative embodiment in accordance with the invention of an ultrasound sheath for medical diagnostic instruments.

In FIG. 6, a sheath 40, which is similar to the sheath 30 of FIG. 5, is fitted with cuffs 32 that extend from both ends of the active transducer portion. A separate elastic band 42 is placed over the cuff, which may be elastic or inelastic. The elastic band 42 overlays the end of the cuff 32 and also extends to overlay a portion of the shaft 24 of the endoscope 22. The elastic band 42 is stretched to fit on the shaft 24 and over the cuff 32 such that when released, the elastic band 42 contracts and tightly holds the sheath 40 in position o the shaft 24. An elastic band 42 is used on one or both longitudinal ends of the sheath 40.

In each embodiment of FIGS. 5 and 6, the balloon alternatives may also be applied as illustrated in FIGS. 3 and 4. In each embodiment, the sheath is attachable to a standard endoscope shaft and is removable and disposable. The transducer may be manufactured inexpensively by known techniques, and disposal of the ultrasonic sheath after use presents no economic hardship. More elemental prior art instruments are easily and economically upgraded with ultrasound capability.

Figure 7:
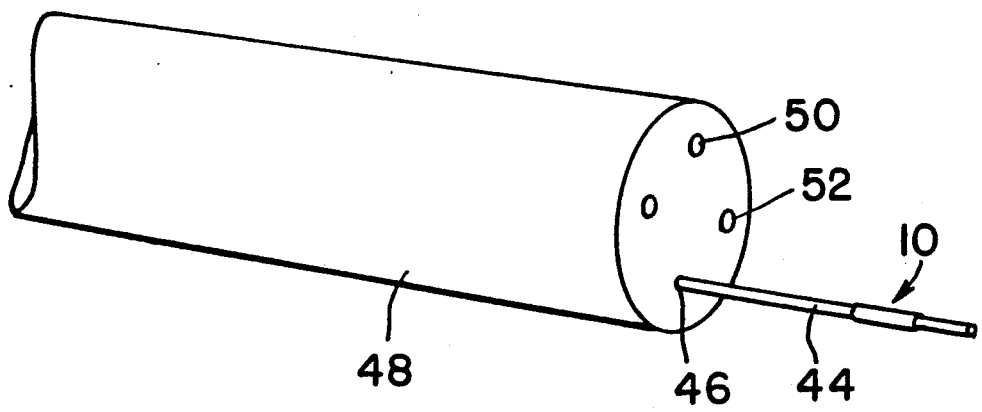
FIG. 7, illustrates a catheter including an ultrasound sheath for medical diagnostic instruments in accordance with the invention as applied to an endoscope.

FIG. 7 illustrates an ultrasonic sheath 10 mounted on a shaft 44 that is extendible from the working channel 46 of an endoscope 48. The endoscope also includes an optical detector 50 and light sources 52. The sheath 10 used in the endoscope 48 may also be fitted with a balloon as illustrated in FIGS. 3 and 4.

Whereas the electrodes are described above as being gold, other electrically conductive materials compatible with usage within the body may be used.

In another alternative embodiment (not shown), the core 11 is omitted. The two electrode layers 12, 16 are formed respectively on the inside and outside of the piezoelectric layer 14 with leads 20 connected as described above. The transducer is slid along the instrument shaft to the desired location. This transducer may also be adapted for use with a balloon, cuffs, elastic bands, etc., as described above.

Although the core 11 has been described above as relatively rigid, it should be understood that in alternative embodiments in accordance with the invention, the core may be any electrically non-conductive material that reflects rather than transmits or absorbs the major portion of the ultrasound energy at its interface with the piezoelectric material and electrodes.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limited sense. It should also be understood that the following claims are intended to cover all of the generic and specific features of the invention herein described and all statements of the scope of the invention that may be said to fall therebetween.

We claim:

1. A disposable ultrasound transducer sheath for removable attachment at a particular location to the external surface of the shaft of a medical diagnostic instrument, comprising:

a cylindrical core having a central opening and an outer surface aligned to a core axis, said central opening being contoured and dimensioned in cross sections in correspondence with and for substantially encircling the external surface of said shaft at said particular location, said core being electrically non-conductive;

a cylindrical piezoelectric layer having an inner surface and an outer surface formed over and substantially encircling said core outer surface;

a first electrically conductive layer sandwiched between said piezoelectric layer and said outer surface of said core, said first conductive layer being in surface contact with and substantially encircling said core outer surface and being in surface contact with said piezoelectric layer inner surface; and a second conductive layer formed over said piezoelectric layer, said second conductive layer being in surface contact with and substantially encircling said outer surface of said piezoelectric layer.

2. A disposable ultrasound transducer sheath as in claim 1, wherein said piezoelectric layer is at least one of resilient and flexible.

3. A disposable ultrasound transducer sheath as in claim 2, wherein one of said first and second conductive layers substantially continuously contacts the adjacent piezoelectric layer surface and the other one of said first and second conductive layers includes a plurality of conductive strips aligned with said axis and separated one from the other, said conductive strips being in contact with said piezoelectric layer.

4. A disposable ultrasound transducer sheath as in claim 1, wherein said piezoelectric element is formed of polyvinylidene fluoride.

5. A disposable ultrasound transducer sheath as in claim 1, wherein said conductive layers are formed of gold.

6. A disposable ultrasound transducer sheath as in claim 3, and further comprising electrical leads extending respectively from said conductive layers, each said conductive strip being connected to an electrical lead.

7. A disposable ultrasound transducer sheath as in claim 1, wherein the interface between said piezoelectric layer and said first conductive layer and core is acoustically reflective.

8. A disposable ultrasound transducer sheath for removable attachment at a particular location to the shaft of a medical diagnostic instrument, comprising:
   a core having a central opening and an outer surface aligned to a core axis, said central opening being contoured and dimensioned in cross sections in correspondence with the cross section of said shaft at said particular location, said core being electrically non-conductive;
   a piezoelectric layer having an inner surface and a outer surface formed over said core outer surface, said piezoelectric layer being in the order of approximately 5 to 15 microns in thickness;
   a first electrically conductive layer sandwiched between said piezoelectric layer and said outer surface of said core, said first conductive layer being in surface contact with said core outer surface and with said piezoelectric layer inner surface; and
   a second conductive layer formed over said piezoelectric layer, said second conductive layer being in surface contact with said outer surface of said piezoelectric layer.

9. A disposable ultrasound transducer sheath for removable attachment at a particular location to the shaft of a medical diagnostic instrument, comprising:
   a core having a central opening and an outer surface aligned to a core axis, said central opening being contoured and dimensioned in cross sections in correspondence with the cross section of said shaft at said particular location, said core being electrically non-conductive, said core being dimensioned to fit onto said shaft at said particular location with a tight frictional fit between them;
   a piezoelectric layer having an inner surface and a outer surface formed over said core outer surface;
   a first electrically conductive layer sandwiched between said piezoelectric layer and said outer surface of said core, said first conductive layer being in surface contact with said core outer surface and with said piezoelectric layer inner surface; and
   a second conductive layer formed over said piezoelectric layer, said second conductive layer being in surface contact with said outer surface of said piezoelectric layer.

10. A disposable ultrasound transducer sheath for removable attachment at a particular location to the shaft of a medical diagnostic instrument, comprising:
    a core having a central opening and an outer surface aligned to a core axis, said central opening being contoured and dimensioned in cross sections in correspondence with the cross section of said shaft at said particular location, said core being electrically non-conductive;
    a piezoelectric layer having an inner surface and a outer surface formed over said core outer surface;
    a first electrically conductive layer sandwiched between said piezoelectric layer and said outer surface of said core, said first conductive layer being in surface contact with said core outer surface and with said piezoelectric layer inner surface;
    a second conductive layer formed over said piezoelectric layer, said second conductive layer being in surface contact with said outer surface of said piezoelectric layer; and
    an elastic cuff extending axially from at lest one of said core and said piezoelectric layer, said cuff being subject to elastically stretching when said transducer is positioned on said instrument shaft at said particular location, said elastic stretching bringing said cuff into compressive contact with said shaft, thereby holding said transducer in place.

11. A disposable ultrasound transducer sheath for removable attachment at a particular location to the shaft of a medical diagnostic instrument, comprising:
    a core having a central opening and an outer surface aligned to a core axis, said central opening being contoured and dimensioned in cross sections in correspondence with the cross section of said shaft at said particular location, said core being electrically non-conductive;
    a piezoelectric layer having an inner surface and a outer surface formed over said core outer surface;
    a first electrically conductive layer sandwiched between said piezoelectric layer and said outer surface of said core, said first conductive layer being in surface contact with said core outer surface and with said piezoelectric layer inner surface;
    a second conductive layer formed over said piezoelectric layer, said second conductive layer being in surface contact with said outer surface of said piezoelectric layer;
    a cuff extending axially from at least one of said core and piezoelectric layer, said cuff being subject to at least partially encircling said instrument shaft when said transducer is applied to said instrument, and
    an elastic band for overlying said cuff, said band being subject to elastically stretching when said band is positioned over said cuff on said transducer when said transducer is positioned at said particular location on said instrument shaft, said elastic stretching bringing said cuff into compressive contact with said shaft, thereby holding said transducer in place.

12. A disposable ultrasound transducer sheath for removable attachment at a particular location to the shaft of a medical diagnostic instrument, comprising:
    a core having a central opening and an outer surface aligned to a core axis, said central opening being contoured and dimensioned in cross sections in correspondence with the cross section of said shaft at said particular location, said core being electrically non-conductive and having a thickness in the range of 150 to 250 microns,
    a piezoelectric layer having an inner surface and a outer surface formed over said core outer surface;
    a first electrically conductive layer sandwiched between said piezoelectric layer and said outer surface of said core, said first conductive layer being in surface contact with said core outer surface and with said piezoelectric layer inner surface; and a second conductive layer formed over said piezoelectric layer, said second conductive layer being in surface contact with said outer surface of said piezoelectric layer.

13. A disposable ultrasound transducer sheath for removable attachment at a particular location to the shaft of a medical diagnostic instrument, comprising:
   a core having a central opening and an outer surface aligned to a core axis, said central opening being contoured and dimensioned in cross sections in correspondence with the cross section of said shaft at said particular location, said core being electrically non-conductive;
   a piezoelectric layer having an inner surface and a outer surface formed over said core outer surface;
   a first electrically conductive layer sandwiched between said piezoelectric layer and said outer surface of said core, said first conductive layer being in surface contact with said core outer surface and with said piezoelectric layer inner surface;
   a second conductive layer formed over said piezoelectric layer, said second conductive layer being in surface contact with said outer surface of said piezoelectric layer; and
   a reversibly inflatable balloon coaxially surrounding said transducer.

14. A disposable ultrasound transducer sheath for removable attachment at a particular location to the shaft of a medical diagnostic instrument, comprising:
   an annular piezoelectric layer having an inner and outer surface aligned to an axis, said piezoelectric layer being at least one of resilient and flexible;
   a first electrically conductive layer in surface contact with said piezoelectric layer inner surface; and
   a second conductive layer formed over said piezoelectric layer, said second conductive layer being in surface contact with said outer surface of said piezoelectric layer, one of said first and second conductive layers substantially continuously contacting the adjacent piezoelectric layer surface, and the other one of said conductive first and second layers includes a plurality of conductive strips aligned with said axis and separated one from the other, said conductive strips being in contact with said piezoelectric layer.

15. A disposable ultrasound transducer sheath as in claim 14, wherein said piezoelectric element is formed of polyvinylidene fluoride.

16. A disposable ultrasound transducer sheath as in claim 15, wherein said conductive layers are formed of gold.

17. A disposable ultrasound transducer sheath as in claim 14, wherein said conductive layers are formed of gold.

18. A disposable ultrasound transducer sheath as in claim 14, wherein said piezoelectric layer in the order of approximately 5 to 15 microns in thickness.

19. A disposable ultrasound transducer sheath as in claim 14, wherein the interface between said piezoelectric layer and said first conductive layer is acoustically reflective.

20. A disposable ultrasound transducer sheath as in claim 14, and further comprising an elastic cuff extending axially from said piezoelectric layer, said cuff being subject to elastically stretching when said transducer is positioned on said instrument shaft at said particular location, said elastic stretching bringing said cuff into compressive contact with said shaft, thereby holding said transducer in place.

21. A disposable ultrasound transducer sheath as in claim 14, and further comprising a cuff extending axially from said piezoelectric layer, said cuff being subject to at least partially encircling said instrument shaft when said transducer is applied to said instrument, and further comprising an elastic band for overlying said cuff, said band being subject to elastically stretching when said band is positioned over said cuff when said transducer is positioned at said particular location on said instrument shaft, said elastic stretching bringing said cuff into compressive contact with said shaft, thereby holding said transducer in place.

22. A disposable ultrasound transducer sheath as in claim 14, and further comprising a reversible inflatable balloon coaxially surrounding said transducer.

23. A disposable ultrasound transducer sheath for removable attachment at a particular location to the shaft of a medical diagnostic instrument, comprising:
   an annular piezoelectric layer having an inner and an outer surface aligned to an axis;
   a first electrically conductive layer in surface contact with said piezoelectric layer inner surface;
   a reversibly inflatable balloon coaxially surrounding the outer surface of said piezoelectric layer; and
   a second conductive layer formed over said inflatable balloon, said second conductive layer being in surface contact with the outer surface of said balloon.

24. A disposable ultrasound transducer sheath as in claim 23, wherein one of said conductive layers is a continuous surface of the other said conductive layer is a plurality of conductive strips aligned with said axis and separated one from the other.

25. A disposable ultrasound transducer sheath as in claim 24, further comprising electrical leads extending respectively from said conductive layers, each said conductive strip being connected to an electrical lead.

26. A disposable ultrasound transducer sheath for removable attachment at a particular location to the shaft of a medical diagnostic instrument, comprising:
   a core having a central opening and an outer surface aligned to a core axis, said central opening being contoured and dimensioned in cross sections for correspondence with the cross section of said shaft at said particular location, said core being electrically non-conductive;
   a piezoelectric layer having an inner surface and a outer surface formed over said core outer surface, said piezoelectric layer being at least one of resilient and flexible;
   a first electrically conductive layer sandwiched between said piezoelectric layer and said outer surface of said core, said first conductive layer being in surface contact with said core outer surface and with said piezoelectric layer inner surface;
   a second conductive layer formed over said piezoelectric layer, said second conductive layer being in surface contact with said outer surface of said piezoelectric layer, one of said first and second conductive layers substantially continuously contacts the adjacent piezoelectric layer surface and the other one of said first and second conductive layers includes a plurality of conductive strips aligned with said axis and separated one from the other, said conductive strips being in contact with said piezoelectric layer;

electrical leads extending respectively from said conductive layers, each said conductive strip being connected to an electrical lead.

27. A disposable transducer for removable attachment at a particular location to the external surface of the shaft of a medical diagnostic instrument, comprising:

a transducer unit including a transducer, said transducer unit being dimensioned to rest, in use, on a particular location of said shaft surface;

an elastic cuff extending from said transducer unit, said cuff being an elastic loop and subject to stretching in use to encircle said instrument shaft proximate said particular location, said elastic stretching bringing said cuff into compressive contact with said shaft, thereby holding said transducer in place.

28. A disposable transducer for removable attachment at a particular location to the external surface of the shaft of a medical diagnostic instrument, comprising:

a transducer unit including a transducer, said transducer unit being dimensioned to rest, in use, on a particular location of said shaft surface;

a cuff extending from said transducer unit, said cuff in use of said instrument being subject to at least partially encircling said instrument shaft;

an elastic band for overlying said cuff, said band being subject to elastic stretching when sand band is positioned over said cuff when said transducer is positioned at said particular location on said instrument shaft, said elastic stretching of said band bringing said cuff into compressive contact with said shaft, thereby holding said transducer in place.

* * * * *